United States Patent [19]
Allen

[11] Patent Number: 5,097,839
[45] Date of Patent: * Mar. 24, 1992

[54] APPARATUS FOR IMAGING THE ANATOMY

[76] Inventor: George S. Allen, 628 Westview Ave., Nashville, Tenn. 37205

[*] Notice: The portion of the term of this patent subsequent to Mar. 10, 2009 has been disclaimed.

[21] Appl. No.: 479,262

[22] Filed: Feb. 13, 1990

Related U.S. Application Data

[62] Division of Ser. No. 223,975, Jul. 18, 1988, Pat. No. 4,945,914.

[51] Int. Cl.$^5$ .............................................. A61B 6/03
[52] U.S. Cl. ................................. 128/653.1; 606/130; 378/901
[58] Field of Search ........ 128/653 R, 653 A, 653 SC, 128/659; 606/130; 364/413.16, 413.18, 413.22; 378/910; 382/6

[56] References Cited

U.S. PATENT DOCUMENTS

| | | | |
|---|---|---|---|
| 4,086,492 | 4/1978 | Lodge et al. | 378/901 |
| 4,341,220 | 7/1982 | Perry | 128/630 |
| 4,465,069 | 8/1984 | Barbier et al. | 128/303 B |
| 4,572,198 | 2/1986 | Codrington | 128/653 |
| 4,580,561 | 4/1986 | Williamson | 128/303 B |
| 4,583,538 | 4/1986 | Onik et al. | 128/303 B |
| 4,608,635 | 8/1986 | Osterholm | 378/901 |
| 4,629,451 | 12/1986 | Winters et al. | 128/303 B |
| 4,638,798 | 1/1987 | Shelden et al. | 128/653 |
| 4,667,660 | 5/1987 | Eingorn | 128/303 B |
| 4,674,046 | 6/1987 | Ozeki et al. | 364/413.16 |
| 4,710,716 | 12/1987 | Keren et al. | 128/653 A |
| 4,769,756 | 9/1988 | Webber et al. | 364/413.16 |
| 4,774,957 | 10/1988 | Nambu et al. | 128/653 |
| 4,777,598 | 10/1988 | Kellar et al. | 364/413.22 |
| 4,791,934 | 12/1988 | Brunnett | 128/653 R |
| 4,838,264 | 6/1989 | Bremer et al. | 128/303 B |

FOREIGN PATENT DOCUMENTS

0955916  9/1982  U.S.S.R. .............................. 128/303 B

OTHER PUBLICATIONS

Winter et al., "Microwave Hyperthemia for Brain Tumors", *Neurosurgery*, vol. 17, No. 3, pp. 387-399 (1985).
"A Dedicated CT System For The Sterotactic Operating Room", by L. Lunsford, Appl. Neurophysiol. 45: 374-378 (1982).
"A Sterotaxic Apparatus for Intercerebral Surgery", by Lars Leksell, Dept. of Neurotraumatology, Serafimerlasarettet, Stockholm.

*Primary Examiner*—Ruth S. Smith
*Attorney, Agent, or Firm*—Kenyon & Kenyon

[57] ABSTRACT

The present invention pertains to a fiducial implant for the human body that is detectable by an imaging system. The invention is comprised of a first portion and a second portion. The first portion is configured to be detected by an imaging system when placed beneath the skin. The second portion is configured for fixed attachment to a bone beneath the skin without penetrating entirely through the bone and without fracturing the bone. The first portion is of detectable size and comprised of a material for detection by an imaging system, and sufficiently small to avoid the distortion of the skin when placed at an interface between the skin and the bone. The first portion also has at least a portion which is spherical and defines a surface for cooperating with a tool for securing the second portion to the bone. Additionally, the placement of n fiducial implants, where $n \geq 4$ and is an integer, into a portion of anatomy of the human body allows for the recreation of a particular image slice of the portion of the anatomy taken by an imaging system with respect to a first time period, at subsequent imaging sessions and also with different scan modalities. This provides a doctor with the ability to accurately follow the progress of the portion of the anatomy of interest. Moreover, the existence of n fiducial implants allows a target to be identified within the portion of anatomy relative to an external coordinate system. The portion of anatomy with the target may then be operated on, for instance, robotically, or precisely irradiated.

2 Claims, 5 Drawing Sheets

APPARATUS FOR IMAGING THE ANATOMY

This application is a division of application Ser. No. 07/223,975 filed July 18, 1988 U.S. Pat. No. 4,945,914.

BACKGROUND AND DISCUSSION OF THE INVENTION

Diagnostic techniques that allow the practicing clinician to obtain high fidelity views of the anatomical structure of a human body have proved helpful to both the patient and the doctor. Imaging systems providing cross-sectional views such as computed tomographic (CT) x-ray imagers or nuclear magnetic resonance (NMR) machines have provided the ability to improve visualization of the anatomical structure of the human body without surgery or other invasive techniques. The patient can be subjected to scanning techniques of such imaging systems, and the patient's anatomical structure can be reproduced in a form for evaluation by a trained doctor.

The doctor sufficiently experienced in these techniques can evaluate the images of the patient's anatomy and determine if there are any abnormalities present. An abnormality in the form of a tumor appears on the image as a shape that has a discernible contrast with the surrounding area. The difference in contrast is due to the tumor having different imaging properties than the surrounding body tissue. Moreover, the contrasting shape that represents the tumor appears at a location on the image where such a shape would not normally appear with regard to a similar image of a healthy person.

Once a tumor has been identified, several methods of treatment are utilized to remove or destroy the tumor including chemotherapy, radiation therapy and surgery. When chemotherapy is chosen drugs are introduced into the patient's body to destroy the tumor. During the course of treatment, imagers are commonly used to follow the progress of treatment by subjecting the patient to periodic scans and comparing the images taken over the course of the treatment to ascertain any changes in the tumor configurations.

In radiation therapy, the images of the tumor generated by the imager are used by a radiologist to adjust the irradiating device and to direct radiation solely at the tumor while minimizing or eliminating adverse effects to surrounding healthy tissue. During the course of the radiation treatment, the imaging system is also used to follow the progress of the patient in the same manner described above with respect to chemotherapy.

When surgery is used to remove a tumor, the images of the tumor in the patient can guide the surgeon during the operation. By reviewing the images prior to surgery, the surgeon can decide the best strategy for reaching and excising the tumor. After surgery has been performed, further scanning is utilized to evaluate the success of the surgery and the subsequent progress of the patient.

A problem associated with the scanning techniques mentioned above is the inability to select and compare accurately the cross section of the same anatomical area in images that have been obtained by imagers at different times or by images obtained essentially at the same time using different image modalities, e.g., CT and MRI. The inaccuracy in image comparison can be better appreciated from an explanation of the scanning techniques and how the imaging systems generate the images within a cross-sectional "slice" of the patient's anatomy. A slice depicts elemental volumes within the cross-section of the patient's anatomy that is exposed or excited by the radiation beam or a magnetic field and the information is recorded on a film or other tangible medium. Since the images are created from slices defined by the relative position of the patient with respect to the imager, a change of the orientation of the patient results in different elemental volumes being introduced into the slice. Thus, for comparison purposes two sets of image slices of approximately the same anatomical mass taken at different times do not provide comparable information that can be accurately used to determine the changes that occurred between two image slices in the sets, since it is unknown to what extent the two individual image slices selected from the respective sets depict identical views.

The adverse effects on the medical practice of such errors is exemplified by diagnostic techniques utilized by the surgeon or others in diagnosing a tumor within a patient. If a patient has a tumor, its size density and location can be determined with the help of images generated by a scanning device. For the clinician to make an assessment of the patient's treatment, two scanning examinations are required. The patient is subjected to an initial scan that generates a number of slices through the portion of the anatomy, for instance the brain, to be diagnosed. During scanning, the patient is held in a substantially fixed position with respect to the imager. Each slice of a particular scan is taken at a predetermined distance from the previous slice and parallel thereto. Using the images of the slices, the doctor can evaluate the tumor. If, however, the doctor wants to access changes in the configuration of the tumor over a given period of time, a second or "follow-up" scan has to be taken.

The scanning procedure is repeated, but since the patient may be in a position different from that in the original scan, comparison of the scans is hampered. Slices obtained at the follow-up examination may be inadvertently taken at an angle when compared to the original slices. Accordingly the image created may depict a larger volume than that which was actually depicted before. Consequently, the surgeon may get a false impression of the size of the tumor when comparing scans taken at different periods. Because of this, slice-by-slice comparison cannot be performed satisfactorily.

Similarly for certain surgical techniques it is desirable to have accurate and reliable periodic scans of identical segments of the tumor within the cranial cavity. If the scans before and after surgery are inaccurate, the doctor may not get the correct picture of the result of surgery. These same inaccuracies apply to other treatments such as chemotherapy discussed above.

Additionally, with regard to imaging systems and the integral part they play in surgical and other tumor treatment procedures, there is a dearth of methods currently existing that allow a determination of a desired location within the body at a given time. For example, U.S. Pat. No. 4,583,538 to Onik, et. al. discloses a localization device that is placed on a patient's skin which can be identified in a slice of a CT scan. A reference point is chosen from a position on the device which exactly correlates to a point on the CT scan. Measurements of the localization device on the CT scan is then correlated to the device on the patient.

Exterior devices have been utilized in an attempt to solve some of these problems with accuracy such as that shown in U.S. Pat. No. 4,341,220 to Perry which discloses a frame that fits over the skull of a patient. The frame has three plates, each defining a plurality of slots on three of four sides. The slots are of varying lengths and are sequentially ordered with respect to length. Frame coordinates defined and found on the frame correspond to the varying heights of the slots. When slices of the skull and brain are taken by an imaging device, the plane formed by the slice intersects the three plates. The number of full slots in the slice are counted with respect to each plate to determine the coordinate of a target site with the brain. Accordingly, only one CT scan is needed to pinpoint the coordinates of the target.

Other attempts have included the use of catheters for insertion into the anatomy. For example, U.S. Pat. No. 4,572,198 to Codrington discloses a catheter with a coil winding in its tip to excite or weaken the magnetic field. The weak magnetic field is detectable by an NMR device thus pinpointing the location of the catheter tip with respect to the NMR device.

Applicant's invention largely overcomes many of the deficiencies noted above with regard to imagers used heretofore. The invention relates to a method and apparatus for insuring that scans taken at different times produce images substantially identical to those of previous scans even if they are from different image modalities at different times. This insures that a more accurate assessment at any changes in anatomy is obtained. As a result, the doctor can be more certain as to the size, location and density of the tumor, or a section thereof, that is located in the cranial cavity.

This ability will enhance the use of surgical techniques in removing or otherwise eliminating the tumor in particular by those noninvasive techniques such as laser technology. By having the ability to define accurately the tumor location and size, laser beams can be focused directly on the tumor. Intermittently, as part of surgical techniques, scans can be made to determine if the tumor has moved or substantially changed in size as a result of the surgery. The laser or other surgical instrument can be adjusted accordingly. Because of the accuracy of the imaging techniques produced by the invention, the doctor can be confident that the amount of healthy tissue destroyed during surgery is minimized.

A method adopted by the invention disclosed herein utilizes fiducial implants or implants to define a plane which corresponds with the images, or other computer, and particularly the data processing capabilities of the image to insure that subsequent scanning results in slices substantially parallel to those taken during the initial scan. The fiducial implants are implanted beneath the skin into the calvaria and are spaced sufficiently from one another to define a plane. The patient with these implants implanted is placed in the scanning device in the conventional manner and scanned to provide the images of consecutive parallel slices of a given thickness along a predetermined path through the cranial cavity.

As the scans are taken, one or more slices will be needed to accommodate part or all of each fiducial implant. The computational features of the imager or other computer will take into account the spatial relationship between any selected plane of a slice and that plane defined by the fiducial implants. Because of this capability, images taken in subsequent scans at different points in time, at different angles can be reconstructed to be substantially identical with the slices taken originally.

Fiducial implants for this purpose are specially configured and made of material that enables their implantation into the skull and the ability to be detected by scanning devices. The fiducial implant as disclosed herein is configured to insure that during implantation it does not have adverse effects on the skull such as cracking or extending through to the cranial cavity. Nor is it sufficiently exposed between the skull and the skin to distort any external features of the anatomy. Furthermore, the fiducial implant is positioned at least on a portion of the skull at the interface of the skin and the bone of the skull to facilitate its imaging by the imager. At least a portion of the implant is symmetrical in cross-section such that slices taken of the cranial cavity for example can be used to locate the center of mass of the implant. This insures accuracy in using the implant image as a reference point to transform the subsequent slices of the follow-up examination into the proper position and orientation.

The above has been a description of certain deficiencies in the prior art and advantages of the invention. Other advantages may be perceived from the detailed description of the preferred embodiment which follows.

BRIEF DESCRIPTION OF THE DRAWINGS

A more complete appreciation of the present invention and many of the attendant advantages thereof will be readily obtained, as the same becomes better understood by reference to the following detailed description, when considered in connection with the accompanying drawings, wherein.

DESCRIPTION OF THE PREFERRED EMBODIMENT

Figure 1A:
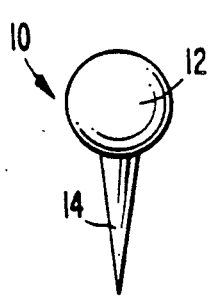
FIGS. 1a, 1b, and 1c show side and overhead views of fiducial implants.
Figure 1B:
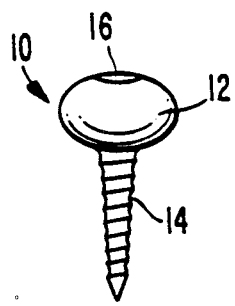
Figure 1C:
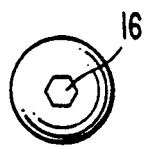

In FIG. 1, there is shown a fiducial implant 10 for the human body that is detectable by an imaging system. The fiducial implant comprises a first portion 12 and a second portion 14. The first portion 12 is configured to be detected by an imaging system (when placed beneath the skin.) The second portion 14 is configured for fixed attachment to the bone beneath the skin without penetrating entirely through the bone and without fracturing the bone, as will be described in more detail later. The first portion 12 is of detectable size and comprised of a material for detection by an imaging system and sufficiently small to provide minimal distortion of the skin when placed at an interface between the skin and the bone as will be described in more detail later. First portion 12 also has at least a portion which is spherical and defines a surface for cooperating with a tool for securing the second portion 14 to the bone. Additionally, the placement of three fiducial implants 10 into a portion of anatomy of the human body allows for the recreation of a particular image slice of the portion of the anatomy taken by an imaging system in order to duplicate images taken at the first time period, that is, at the initial examination. This provides a doctor with the ability to accurately follow the progress of treatment on selected slices representing the anatomy of interest.

Moreover, the existence of three fiducial implants 10 allows a target (a tumor for instance) to be identified relative to an external coordinate system. The portion of anatomy with the target may then be operated on, for instance, robotically, or precisely irradiated.

To allow for the accurate comparison of image slices from at least two distinct periods of time, the three fiducial implants 10 are first implanted into a body of a patient at a desired region of interest. The patient is then placed in an imaging system and images of a series of cross-sectional slices are obtained that include, for example, the volume of the tumor which is the primary target of interest. From the imaging data obtained, the three fiducial implants are located and an internal coordinate system is defined with respect to them. If it is so desired, the image data may be further reformatted to show image slices whose direction is different from that obtained originally during the imaging period. Depending on the diagnostic information that these image slices reveal, appropriate decisions with regard to surgery, chemotherapy or radiation therapy on a patient may be made. The imaging data can also be used from several different types of images, such as CT, PET or NMR to obtain the same view of the anatomy but with different qualities stressed.

If it is decided to obtain further imaging data at a later time, then the patient is returned to the imaging system and the procedure for obtaining image data is repeated. The fiducial implants 10 are located with respect to the second imaging session and the same internal coordinate system is defined relative to the implants 10. Once the same internal coordinate system is defined with respect to the second imaging session, the translation and rotation of the internal coordinate system and the images with it is determined with respect to the coordinate system established at the first imaging session. An image slice identified from the first imaging session that is to be used for diagnosis, is recovered from the second imaging session. The two image slices, one from the first image session and one from the second image session, are then compared to determine what changes, if any, have occurred in the anatomy of the patient.

The following discussion relates to the three dimensional non-collinear coordinate system defined by three distinct non-collinear points. In referring to such a system, it is understood that a three dimensional coordinate system requires three non-coplanar vectors. This is of course achieved with three non-coplanar points. A vector orthogonal to a plane defined by two vectors (three non-collinear points) can be obtained through the cross product of the planar vectors. It should be understood that the vectors are normalized.

More specifically, a 3-dimensional noncollinear coordinate system requires three distinct noncollinear points to be fully defined. If there are more than three identifiable points, the system is over-determined and three points have to be chosen to define the coordinate system. If there are less than three identifiable distinct points, the system is undetermined and a position relative to the one or two identifiable points will not be defined.

The known location of three distinct points identifies a plane upon which an orthogonal coordinate system can be established. If the three points are fixed in place relative to each other over time in the body, a coordinate system can be established that is also fixed in time. The ability to define a fixed internal coordinate system to the human body over time has important ramifications. A fully defined internal coordinate system that is fixed in place over time with respect to some location in the body permits comparison of subsequent images of the body taken into imaging systems such as CT scans, NMR scans or PET scans, to name a few. More precisely, these comparisons will allow a diagnostician to see what change, if any, has occurred within the body at a predetermined location.

By utilizing a fixed coordinate system relative to the body, the same coordinates can be compared over time. However, the tissue or body material is not necessarily fixed in place relative to a predetermined set of coordinates over time. After the passage of time, the tissue may have shifted, a change not uncommon following surgery. Nevertheless, the ability to compare various properties (depending on the type of images) of the tissue at the same coordinates and at different times is a great advantage for diagnostic purposes.

In principle, the three points (that are necessary) to define a coordinate system can be chosen in a variety of ways. In one embodiment with respect to the brain or head region, the two ears and a tooth, or the two ears and the nose may comprise the three points. Alternatively, an image slice of the skull could provide a set of points from which the three points would be chosen to create the coordinate system for the body. Preferably, three fiducial points that are implanted into the body, and create high contrast images during scanning, provide the most reliable way to define a coordinate system. Ideally the three points should be in the same approximate area of the body that is under analysis, and also should be identifiable and measurable by different imagery systems, such as CT imagers and NMR imagers.

To create a fully defined coordinate system the detection of three distinct noncollinear fiducial points is required. With respect to creating a fully-defined coordinate system anchored to the human body, the requirement of detection dictates the need that fiducial implants 10 are made of a material that is detectable by a system imaging the human body. The fiducial implant 10 has a first portion 12 that provides means for marking a predetermined position within a body. See FIG. 1. First portion, or marker 12, ideally provide a high contrast in an image compared to the surrounding material. The material marker 12 is made of also provides as little distortion as possible to the image so the appearance of artifacts is kept to a minimum. Marker 12 is also safe for use in the human body and is unobtrusive so no discomfort or self-consciousness is experienced by a wearer.

Marker 12 exhibits symmetrical integrity to facilitate its location by the imaging system. When marker 12 is scanned, the symmetry insures that any plane through the implant provides essentially the same image and the ability to locate its center of mass. The importance of being able to identify the center of the marker 12 lies in the fact that the same exact point can be reproducibly found for use in defining the coordinate system. Error is thus minimized from subsequent recreations of the same coordinate system due to displacement of the coordinate system from a previous alignment. For instance, a sphere is the ideal shape for a marker 12 with respect to symmetrical integrity since the image of any plane of the sphere is always a circle.

By knowing the radius of the spherical object and applying standard algorithms, the center can be determined of the spherical marker 12 from any plane passing through the sphere. The algorithm for determining the center of a sphere may require operator interaction to mark the approximate location of the implant. The center of mass can be determined with successful approximation from the boundary of the circular profile identified through the operator's interaction. For instance, by having information about the density of the fiducial implant's image and assuming it spherical, then scan profiles through its image result in bell-shaped distributions, the boundary points of which can be determined therefrom. From the boundary points the center of mass is computed. This may require additional slices depending on the size of the fiducial implant and its relative position with respect to adjacent slices, particularly when the physical size of the implant exceeds that of the scan slice.

Figure 5:
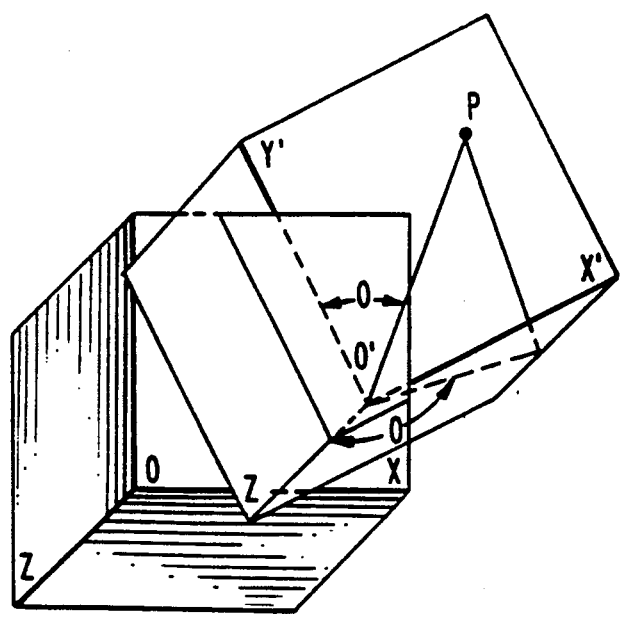
FIG. 5 and FIGS. 5a, 5b and 5c are offset views of two coordinate systems that have undergone translation and rotation with respect to each other.
Figure 5A:
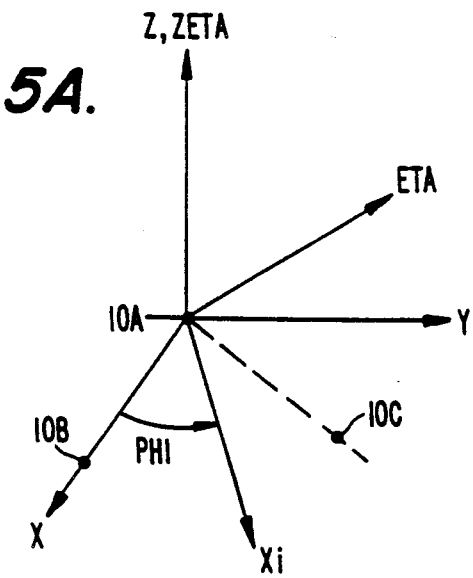

When the centers of mass of the 3 fiducials (10a, 10b, 10c) are determined, then two of them (10a, 10b) define for instance the x-axis vector of the coordinate system and the vector cross product of vectors 10a, 10b and 10a, 10c fully determine the coordinate system as shown in FIG. 5a which is described more fully below.

Marker 12, which is 1 to 10 and preferably 4 millimeters in diameter, can be made of, for example, titanium in the form of a hollow sphere. The hollow of the sphere can be, for example, filled with agarose gel having various desired dopants, the choice of which depends on the imaging system used to best accent or highlight the marker 12. Marker 12 is intimately connected to a second portion, anchor 14, of the fiducial implant 10.

The anchor 14 provides means for anchoring the marker 12 into the body. The site of preference for anchoring the marker 12 in the body is bone, since it provides a good material to hold the implant means in place and also because bone stays in a fixed position over time in the body. Anchor 14 is long enough to penetrate into the bone which it is anchored, and long enough to be firmly embedded without fracturing the bone. Anchor 14 is 1 to 10 and preferably 3 millimeters long. Preferably the anchor 14 should be screwed into the bone, rather than driven with an impact tool to lessen the chance of fracturing the bone. Anchor 14 can also, for example, be made of titanium.

The fiducial implant 10 also has means 16 for receiving force so the anchor 14 can be fixedly secured to the body. Where anchor 14 is a screw, preferably an indentation 16 in the shape of a polygon recess to receive an allen wrench is located in marker 12. The use of an allen wrench with the associated polygonal recess has more symmetrical integrity than the cross shaped receptor site for a phillips screw driver or a single groove receptor site for a standard screw driver.

The implantation of a fiducial implant 10 having an anchor 14, in this case a screw, preferably utilizes a trocar not shown, to penetrate the skin and reach a desired bone site. The trocar is first placed on the skin over the desired anchoring sites and a piercing rod therein is forced through the skin. The piercing rod within the trocar is then removed while the trocar is kept in place. A rod with an allen wrench head fitted to the polygonal indentation 16 in the marker 12 of the implant 10 is inserted into the trocar until the screw 14 portion of the implant 10 contacts the anchoring site, for instance bone. Force is then applied to the portion of the rod extending out the trocar until the implant 10 is embedded into the bone. Such a procedure is accomplished under local anesthesia and should only be about 5 minutes in length.

Figure 2A:
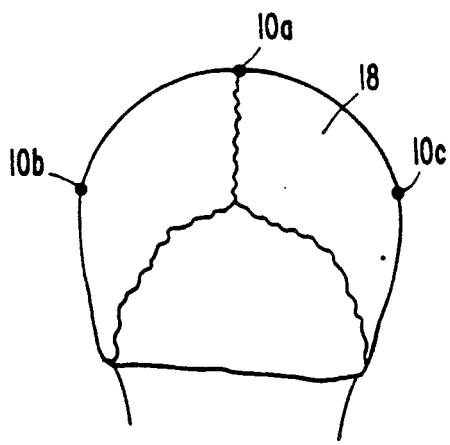
FIGS. 2a and 2b show a side and overhead view of a preferred positioning scheme of fiducial implants in the skull.
Figure 2B:
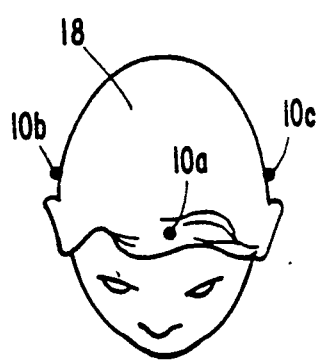

The placement of the three fiducial implants 10 depends on the portion of the anatomy to be evaluated. Essentially, three fiducial implants 10 are placed in three locations such that they are readily identifiable and the locations are fixed with respect to each other over time. If, for example, a study of the skull and brain is to be undertaken, preferably an implant 10A is placed on the midline of the skull 18 just above the hairline, with the other two implants 10B, 10C being placed on the right and left side, respectively, of the midline in a posterior position to the midline implant 10A. See FIGS. 2a and 2b which are a frontal and overhead view of the skull 18, respectively. Another example of an area of interest could be the torso, with one fiducial implant 10 placed on the midline of the sternum and the other two fiducial implants 10 placed laterally thereto on the right and left side, respectively, and in a rib. Or, one fiducial implant 10 can be placed in the spinous process of a vertebra in the midline and the other two fiducial implants placed in the right and left illiac crest, respectively.

The fiducial implants 10 can alternatively be implanted temporarily into a patient in situations where there is only a short term need for their presence. For instance, the method of radiation therapy that is described herein can use either fiducial implants 10 that are implanted permanently into a patient, or temporarily into a patient for the length of time necessary to identify where, for example, a tumor is located within the patient and to align the radiation source to irradiate the tumor.

When the fiducial implants 10 are positioned in a patient on a temporary basis, the same procedure as described above with respect to the permanent placement of the fiducial implants 10 can be used. However, the fiducial implants 10 preferably instead have a second portion 14 which is needle shaped as opposed to the preferably thread second portion 14 in fiducial implants 10 which are permanently placed into a patient. Alternatively, the fiducial implant 10, when it is positioned in a patient on a temporary basis, does not necessarily have to be implanted into bone, as is the preferable anchoring site with respect to the permanent placement of a fiducial implant 10. The fiducial implants 10, when they are positioned in a patient on a temporary basis, are positioned in the patient such that they stay fixed with respect to the patient for the length of time necessary to perform a procedure on the patient that utilizes the internal coordinate system defined by the fiducial implants 10. Thus, the fiducial implants 10 can be implanted into skin or tissue of a patient such that they remain fixed during the time that the procedure, which requires the use of an internal coordinate system with respect to the patient, is being performed. After the procedure is complete, the fiducial implants 10 are removed.

Imaging apparatus provides a fixed axis relative to which any other position in space can be located. As a result, the position of the fiducial marker and the coordinate system these markers define can be located relative to the imaging apparatus. The features of the invention permit the location of the markers relative to the imaging apparatus to be recorded for future reference. In subsequent scans, the patient's orientation may change relative to the imaging apparatus. This new orientation can be measured by locating the fiducial markers in relation to the image apparatus and comparing it to the previously recorded location. The comparison technique permits re-orienting images of subsequent scans to a position corresponding to the earlier recorded scan so that image slices are always at generally the same cross-section of the earlier recorded slices.

In actual operation, these positions are defined by the coordinate system and it is the position of these slices that is changed by translation and rotation as discussed below.

Figure 3:
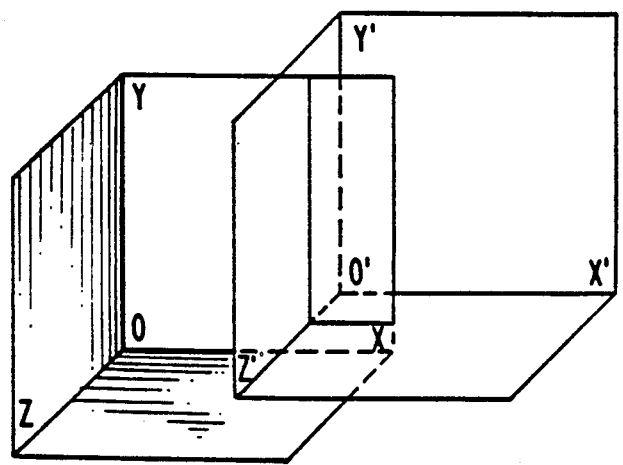
FIG. 3 is an offset view of two coordinate systems that have undergone translation with respect to each other.
Figure 4:
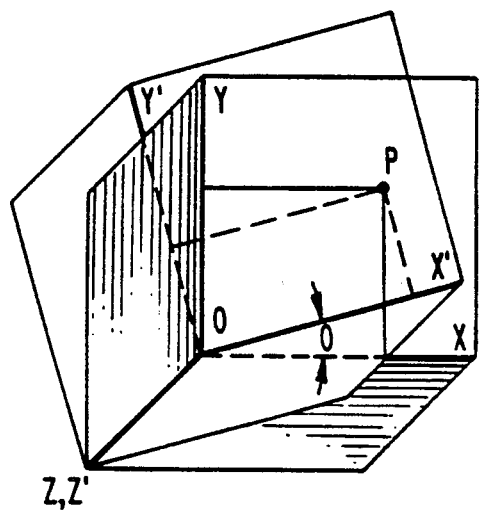
FIG. 4 is an offset view of two coordinate systems that have undergone rotation with respect to each other.

Once the fiducial implants 10 are in place and a coordinate system defined, subsequent images of the same anatomical volume area can be compared. FIGS. 3, 4 and 5 show blocks that represents a person's head for purposes of illustration. If, for example, images of the brain are being taken, a person's head may be placed below, above or to the side (see FIG. 3), of its location at a previous imaging session. The head might be rotated (see FIG. 4), as compared to its orientation during an earlier imaging session. The head might have undergone rotation and translation as compared to a previous imaging session, see FIG. 5. Regardless of the reason why the head is oriented differently, by taking advantage of the fixed fully-defined internal coordinate system in the brain a previous point or slice image of the brain can be obtained from subsequent image information. This is accomplished as shown in FIG. 5, by comparing the location and direction of the plane defined by the three fiducial points at the first examination with the location and direction of the same plane defined by the three fiducial points at the time of the second examination. For simplicity, the origin of the coordinate system is located at a given fiducial point. By measuring the distance in say, the x, y and z directions between the same fiducial point (the origins) at the two different times, the translation of the origin of one coordinate system with respect to the other can be obtained.

Figure 5B:
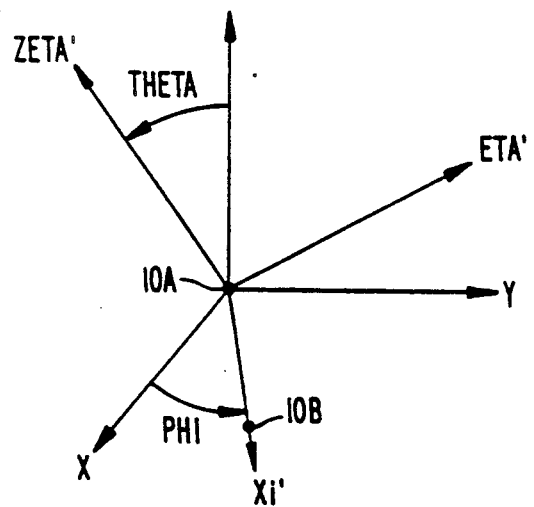
Figure 5C:
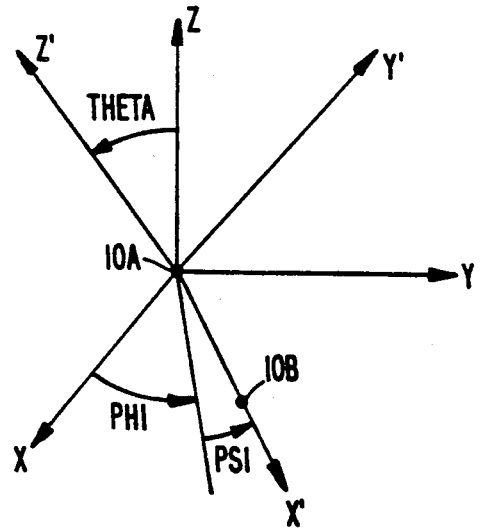

Preferably, one can carry out the transformation with respect to rotation from a given cartesian coordinate system to another by means of three successive rotations performed in a specific sequence. Three angles known as the Eulerian angles are then defined. These three Eulerian angles are the three successful angles of rotation that are required to carry out the transformation. The determination of the Eulerian angles is accomplished by first computing the intersection of two planes determined by the fiducial implants, the computing the angle between the fiducial x-axis and the line of intersection (psi), then computing the angle theta; and then computing the angle phi. At this point the three Eulerian angles are determined. For the example given in FIGS. 5a, 5b and 5c the sequence that is required to carry out the transformation is started by rotating the initial systems of axes, xyz, by an angle phi counterclockwise about the z axis as shown in FIG. 5a (For other transformations, such as those in which a rotation about the Y axis is needed, a different sequence of transformation and rotations can be used). The resultant coordinate system is labelled the xi,eta,zeta axes. In the second stage, the intermediate axes, xi,eta,zeta, are rotated about the xi axis counterclockwise by an angle theta to produce another intermediate set, the xi',eta',zeta' axes as shown in FIG. 5b where the third fiducial implant 10c is not shown to simplify understanding. The xi' axis is at the intersection of the xy and xi'eta' planes and is known as the line of nodes. Finally the xi',eta',zeta' axes are rotated counterclockwise by an angle psi about the zeta' axis to produce the desired x'y'z' system of axes as shown in FIG. 5c. The Eulerian angles theta, phi and psi thus completely specify the orientation of the x'y'z' coordinate system relative to the xyz coordinate system and can therefore act as the three needed generalized coordinates.

The elements of the complete transformation A can be obtained by writing a complete transformation matrix as the triple product of the separate rotations, each of which can be written in matrix form. Thus the initial rotation about the z axis can be described by the matrix D:

$$xi = DX$$

where xi and x stand for column matrices. Similarly, the transformation from xi,eta, zeta, to xi', eta',zeta' can be described by the matrix C:

$$xi' = Cxi$$

and the last rotation to x'y'z' by a matrix B $$x' = Bxi'$$

Thus the matrix of the complete transformation can be written as $$x' = Ax$$

which is the product of the successive matrices:

$$A = BCD$$

The matrix D can be written as $$D = \begin{matrix} \cos\phi & \sin\phi & R \\ -\sin\phi & \cos\phi & R \\ R & R & 1 \end{matrix}$$

The matrix C can be written as $$C = \begin{matrix} 1 & R & R \\ R & \cos\theta & \sin\theta \\ R & -\sin\theta & \cos\theta \end{matrix}$$

The matrix B can be written as $$B = \begin{matrix} \cos\psi & \sin\psi & R \\ -\sin\psi & \cos\psi & R \\ R & R & 1 \end{matrix}$$

The product matrix $A = BCD$ is then obtained with the help of the above expression. The order of the matrix multiplication depends upon the task identified; in the present case it defines the transformation from the xyz set of axes to the x'y'z' set of axes.

Once the Euler angles are determined, the problem of orientation is solved, at least, in principle. A major simplification of the computation can, however, be achieved if Euler's theorem is implemented.

Euler's theorem on the motion of a rigid body states that the general displacement of a rigid body with one point fixed is a rotation about some axis.

If the fixed point is taken as the origin of the body set of axes, then the displacement of the rigid body involves no translation of the body set of axes, the only change is the orientation. The theorem then states that the body set of axes can always be obtained as a single rotation of the initial coordinate system. It is characteristic of rotation that it leaves the direction of rotation unaffected by the operation. In other words, any vector lying in the direction of the axis of rotation must have the same components before and after the rotation. A necessary condition is that the magnitude of the vector should be unaffected and is automatically provided by the orthogonally conditions. Thus Euler's theorem can be proven if it is shown that there exits a vector R having the same component before and after the transformation, that is, in both systems. From this it follows, that $$R' = AR = R$$

The above is an eigenvalue problem that can be written as $$AR - kR = O$$

where k is constant. The values for which k is soluble are called equivalents of the matrix.

The eigenvalue equations may be written $$(A - k1)R = 'R$$

This equation comprises a set of three homogeneous simultaneous equations for the components X,Y,Z of the vector R. Because of this they can never provide the definite values of the three components, only their ratios. Thus the magnitudes of the components remain undetermined. For homogeneous equations the determinant of the above equation has to vanish, and the solution provides the values of k. For the real, orthogonal, matrices the equation must have $k = +1$.

In general the equation has three roots corresponding to three eigenvectors. The consideration lead to diagonal matrix of k $$k = \begin{matrix} k1 & R & R \\ R & k2 & R \\ R & R & k3 \end{matrix}$$

The matrix equation can then be written $$AR = Rk$$

or multiplying from the left by $R^{}(-1)$ $$R^{}(-1)AR = k$$

This equation provides a useful approach to the problem: seek a matrix that transforms A into a diagonal matrix, the elements of which are the desired eigenvalues.

Finally the angle of rotation has to be determined. The direction cosines of the axis of rotation can be obtained by setting $k = 1$ in the eigenvalue equation and solving for the components of R. It can be shown that the trace of the matrix A can be used to determine the angle of rotation W. One has to compute the trace of A, i.e. T, that is, $$T = 1 + \cos W$$

from which W can be determined.

For the rotations described above to have any meaning, the fiducial implant 10A, or some point, must be at the same place for the two coordinate systems that are being aligned. This requires a translation of the fiducial implant 10A at a location corresponding to one coordinate system into the location of fiducial implant 10A at the other coordinate system. By simply moving the desired coordinate system the linear amounts of x, y and z, with respect to a cartesion coordinate system, the fiducial implant 10A is situated at the same location. For a more complete discussion of the transformation of a cartesian coordinate system into another, see Herbert Goldstein, *Classical Mechanics,* Addison Wesley, Reading, Mass., 1965, pp. 107–109.

Thus, any point can be obtained with respect to translation and rotation of a given cartesian coordinate system. Since any point can be obtained, any plane can also be obtained, because a plane is comprised of a set of points. For example, if a given point is desired to be looked at over time, then the coordinate of the point is identified with respect to a first time. The translation and rotation information corresponding to the coordinate system at the first time with respect to the second time is then applied to the point at the first time to indicate the coordinates of the identical point in the coordinate system at the second time. The imaging data pertaining to the second time is then searched to find the desired point. This is but one way of many possible ways to obtain the same point in the coordinate system as a function of time.

Similarly, for a plane or slice image, the same procedure is applied to each point of the set of points that make up the slice image. The desired points are then searched for in the image information corresponding to the coordinate system at the second time. Once all the points, with their associated image information are identified, they are reformatted to produce an image slice as close as possible to the desired image slice pertaining to the coordinate system at the first time. Of course, the position of the slice selected by the physician from the initial image slices has to be determined with respect to the fiducial implants. To this end, preferably, the z coordinates or the elevation coordinates of the system have to be introduced. This can be done with respect to any slice in the image set. For instance, the slice containing the first fiducial implant can be chosen.

Ideally, the reformatting step takes image points from image slices of the second time and aligns them together and produces an image slice as similar as possible to the desired image slice of the first time. In practice, however, quite often a point that is necessary for the creation of a reformatted image does not exist because image slices were taken for instance above and below the point. In this case interpolation must be used to estimate the attributes of the missing point so a desired image slice can be prepared. For example, one simple method of interpolation utilizes the two closest known points to the nonexistent desired point. These two known points are also as nearly opposite each other as possible with the desired point therebetween, and averages their image value. For example, if the intensity of the image associated with one point is 6 units on a scale of 1 to 10 units and that of the second point is 4 units, and the two points are essentially equal in distance from the desired point, the desired point is assigned an image intensity value of 5 units. See FIG. 6 which shows the flow chart describing the above overall process.

Interpolation could be avoided if the internal coordinate system is positioned identically at the different times the imaging data is obtained. This could be accomplished by causing the three fiducial implants 10 to be at exactly the same position whenever imaging data is obtained. By having, for instance, an X-ray machine, or following the method discussed below that reveals the location of the fiducial implants in the body with respect to an external coordinate system, and knowing where the implants were positioned at the first time that imaging occurred, the body could be moved to be in the same exact location. One way of moving the body in position is with a table or platform that has 3 dimensional movement. Then, knowing where the coordinate system is in the body with respect to the platform, the platform could be moved up, down, forward, backward and/or rotated so the internal coordinate system is positioned exactly the same way it was the first time imaging data was obtained.

Figure 6:
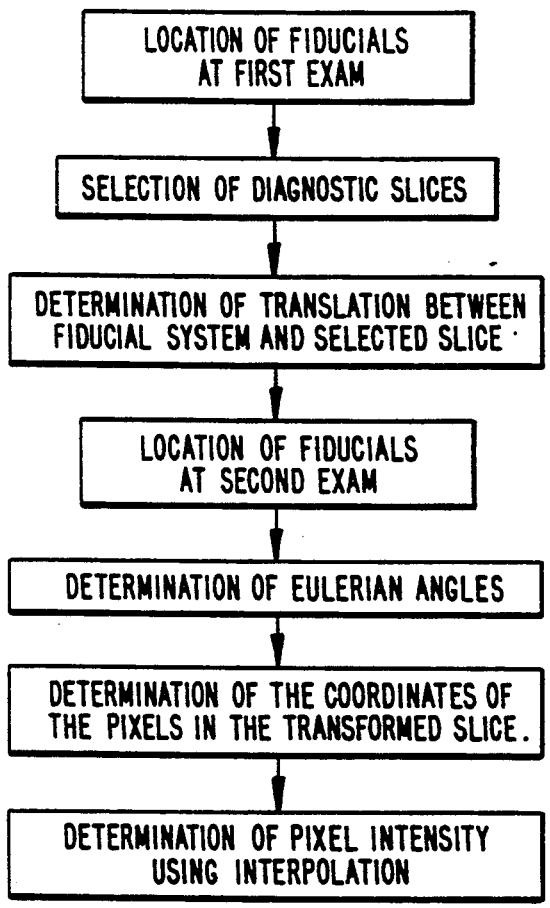
FIG. 6 is a flow chart with respect to determining the same point P at two different times in an internal coordinate system to the body.
Figure 8:
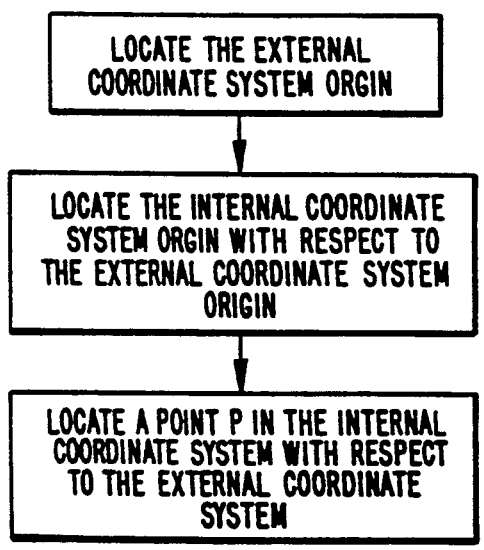
FIG. 8 is a flow chart with respect to determining the location of a point P in an internal coordinate system with respect to an external coordinate system.

To summarize, and referring to FIG. 6, the procedure consists of the following steps:

1. Locating the fiducial implants in the initial examination image set, and establishing the internal coordinate system;
2. Selection of the slice(s) of interest in the initial set;
3. Determination of the translation distance between the coordinate system determined by the fiducial implants and the selected slice;
4. Localization of the fiducial implants in the follow-up study;
5. Determination of Eulerian angles in the coordinate system;
6. Determination of the coordinates of each point in the transformed slice corresponding to the selected slice in the initial system;
7. Determination of the intensity values at each point using interpolation in the axial direction. (Axial direction is defined as the direction of motion of the imager table).

Although there are many different hardware and software embodiments to implement processing of the image data, each can be divided according to its functioning as follows:

(1) hardware that facilitates fast reconstruction of the cross sectional image;
(2) operator-interactive image display;
(3) storage device for images;
(4) hardcopy capability for images.

One embodiment utilizes the existing computer and its peripherals to generate the reformatted images.

Another embodiment utilizes a stand-alone system, in which the images are fed from the respective imager, and then perform the comparative analysis in the stand-along system. The whole computer part of the imager must be essentially duplicated, plus various options for data input supplied, in order to accommodate images of all types. Hardcopy capability is also desirable therein, such as a matrix camera, because permanent records are invaluable to the diagnostician.

Whether a stand-alone system or an existing system is modified for implementation of the above described reformatting, the images are preferably stored as files having two parts: (1) the header that contains the patient's demographic data and information on the examination itself, that is, technical parameters of the exposure or image procedure; and (2) the image matrix. These two parts are preferably stored temporarily (for a couple of days, usually) on magnetic disk drives, and then moved to permanent storage medium, such as magnetic tape or floppy disk. In addition to this file structure a subfile may be added containing the results of the computation (the Euler angles may be added, for instance).

Figure 7:
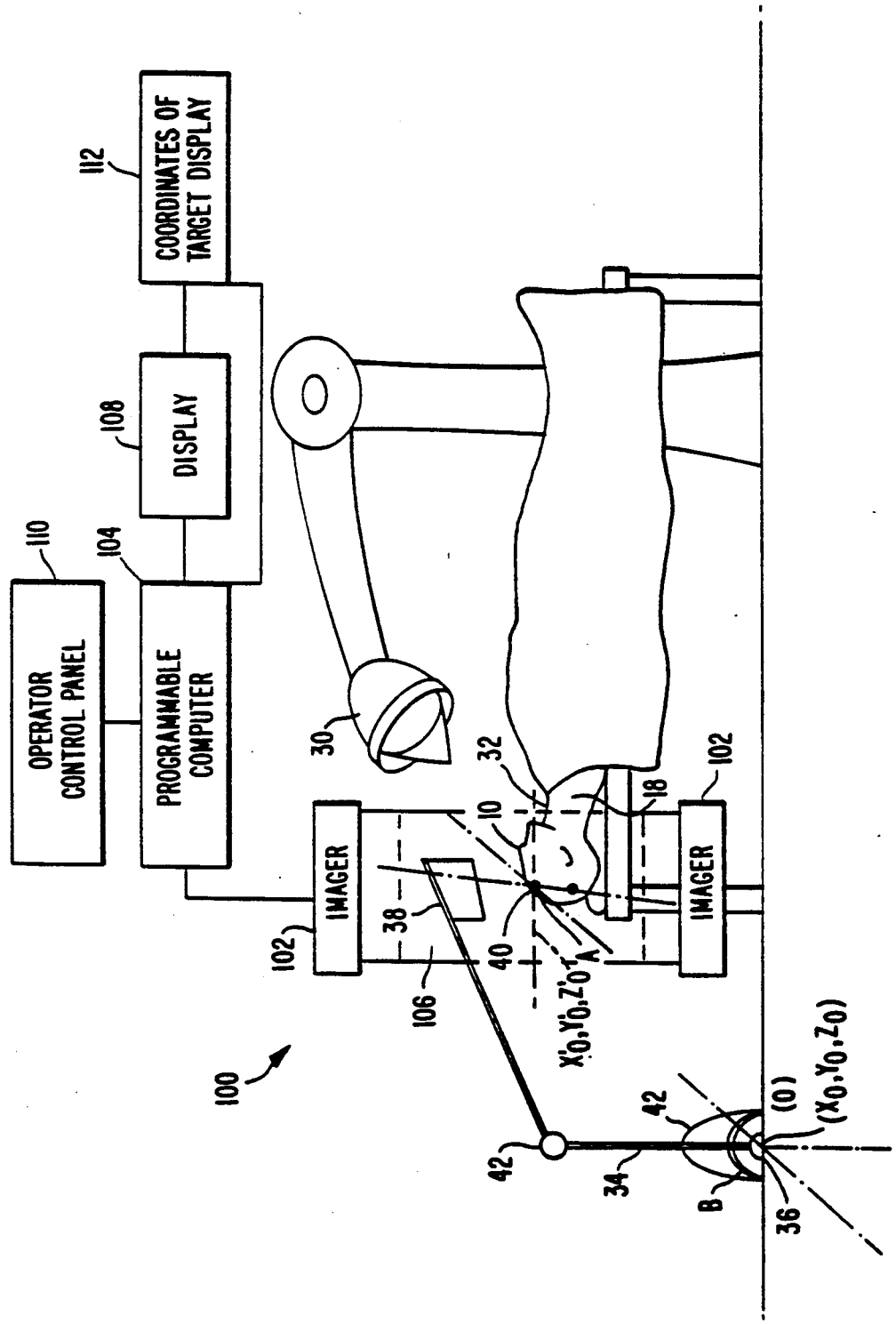
FIG. 7 is a side view of a preferred embodiment of the present invention.

An apparatus 100 carries out the imaging, signal processing and display necessary to provide images of essentially the same coordinates in the human body which can be compared over time, or to provide the location of targets, such as tumors is shown in FIG. 7. Such an apparatus 100 is comprised of an imager 102 that supplies imaging data and is controlled by a programmable computer 104. The imaging data is obtained from a source 106 in the imager 102 that is approximately placed about a patient 107 as is well known in the art. The imaging data experiences signal processing, as described above, and the desired images are displayed on display 108. Additionally, operator interaction can be achieved through an operator control panel 110 and the coordinates of a target can be displayed in the coordinates of the target display 112 for radiation therapy applications.

An application that takes advantage of a fully-defined internal coordinate system of the body relates to radiation therapy. For radiation therapy the location of a radioactive beam of an external coordinate system must be related to the internal coordinate system. See FIG. 5 where the external coordinate system can be considered the unprimed system and the internal system the primed system. The point P can represent the location of a point of a tumor. In this situation the actual distances and locations of the point P in the primed coordinate system, and the location of the origins of the primed coordinate system are important. If the point P is known with respect to the internal or primed coordinate system, and the primed coordinate system is known with respect to the external or unprimed coordinate system and the Euler angles of rotation are known, then the location of point P is known with respect to the external coordinate system. For example and referring to FIG. 7, in radiation therapy or surgery knowing where the internal coordinate system A is with respect to an external coordinate system B has many uses. In radiation therapy if the location of a tumor is known with respect to the internal coordinate system and the internal coordinate system is known with respect to an external coordinate system having a radiation source 20, such as an x-ray machine for killing cancer cells, then radiation can be applied only to the tumor provided it can concentrate on the volume of the tumor only. This would remove the guess work of a radiotherapist looking at various images of a tumor in a body and estimating where to aim the radiation source so, hopefully, only the tumor is irradiated. The location of a tumor in an internal coordinate system can be identified for instance, by a first imaging session. The data therefrom is stored in a medium that allows its recall when the tumor position is desired to be known and it is not desired to have to retake images of the anatomy.

One way to accomplish the irradiation of a specific location in the body 32, where, for instance, a tumor is located, involves the use of a robot arm 34 whose base 36 can be chosen as the origin (0,0,0) of the external coordinate system B. at the tip 38 of the robot arm 34 is located a sensor 40. The sensor 40 can be a metal detector or an ultrasonic detector or any instrument that can sense the position of a fiducial implant 10 in a body 32. If the fiducial implants 10 are placed in a skull 18 and there is a tumor therein, the sensor 40 in the tip 38 of the robot arm 34 is moved by the arm 34 until it contacts a fiducial implant 10 in the skull 18. The movement of the robot arm 34 is tracked by a computer (not shown) so the position of the sensor 40 relative to the arm's 34 base 36, the origin 0 of the external coordinate B, is known. The means to track the arm is well known and is accomplished by sensors (not shown) in critical locations of the arm 34, detecting rotation or movement of the joints 42 of the arm 74. By supplying this information to a computer along with the information of the fixed lengths of the structure of the robot arm 34, the tip 38 location of the arm 34 is always known. When the tip 38 of the arm 34 rests on the fiducial implant 10 in the skull 18, the location of the internal coordinate system A defined by the fiducial implants 10 is known with respect to the external coordinate system B. Supplying the Euler angles of rotation and the location of the tumor which is known relative to the internal coordinate system A to the computer, provides the ability to determine the location of the tumor in the external coordinate system B. The location of the tumor is known relative to the internal coordinate system through for instance the image data already stored, and the fact that the fiducial implants 10 are also fixed relative to each other once they are in place. The radiation source 30 and where it is aimed is known by the computer relative to the external coordinate system B. The computer, having the information where the tumor is located in the external coordinate system B, can aim the radiation source 30 to precisely irradiate the tumor site in the brain. In general, the location of a point P in the internal coordinate system relative to the external coordinate system is determined when the distance between the origins of the two coordinate systems is known and the Euler angles are known, as described above.

In surgery, the internal coordinate system defined by the three fiducial points can allow, for example, a laser to be followed as it cuts through tissue to a tumor. An imaging system present in the operating theater would be positioned to continually take imaging data that is provided to a computer system which also guides the laser based on the inputted data. As the laser cuts through the tissue, the change in the tissue is apparent through the imaging system and can be followed with respect to the fixed internal coordinate system. When a predetermined position is reached by the laser, or a predetermined portion of tissue has been removed by the laser, the computer controlling the laser and processing the imaging data would discontinue the operation of the laser.

In the operation of the invention, after the fiducial implants are in place in a patient, imaging data is taken at a first time and stored. At distinct intervals in time, for instance about every year thereafter, the patient returns to the location of the imaging system or one similar to it, and undergoes follow-up imaging. The most recently received imaging data is then reformatted, as described above, to obtain high fidelity images of the same cross-sections on the body as attained in the earlier session. The images from the latest session are then compared with the earlier session (if there are many earlier sessions they can all be used for comparison purposes) to determine if there have been any significant changes such as progression or regression of an abnormality, such as a tumor. The imaging data collected from various imaging sessions taken at different time intervals can, of course, be compared many ways such as by reformatting images taken at earlier sessions to show an image slice of interest chosen from the latest session, instead of just comparing image slices of a latest session to those of an earlier session. The purpose of the comparisons, as stated earlier can be multifold: (a) either a simple follow-up of the growth of the tumor, without therapy; or (b) verification of therapeutic treatment, such as radiation or chemotherapy or (c) follow-up of surgical treatment.

In the operation of the invention with regard to radiation therapy, the tumor is first identified in the patient's body. The patient is then positioned in the imaging system such that at least the tumor area can be imaged. The imaging system is used to locate the position of the tumor in the internal coordinate system. The image data can, for instance, then be stored for later use so the tumor position is identified without new images having to be obtained every time radiation therapy is performed. The patient can then be placed before a radiation source, and each time radiation therapy occurs, the information from the imaging session that is stored is supplied to the computer operating the radiation source. The internal coordinate is located with respect to the external coordinate system, for instance by locating one fiducial implant, as described above, with respect to a known position in the external coordinate system. Once the position of the internal coordinate system is known with respect to the external coordinate system, the tumor position is known with respect to the external coordinate system, since the tumor position is already known with respect to the internal coordinate system from the stored imaging information. A radiation source is then aimed, for example by a computer receiving the imaging and position data, at the tumor in the body. With respect to surgery, the procedure that is followed to take advantage of the fiducial implants is similar to the procedure described above for radiation therapy. Once the tumor is located with respect to the internal coordinate system, and the location of the internal coordinate system is known with respect to the external coordinate system, the tumor is located with respect to the external coordinate system. Surgical instruments can then be guided to the tumor by the computer with the imaging system placed in an interactive mode therewith. The imaging data that the imaging system constantly feeds the computer allows the computer to track the progress and the extent of the surgery.

In an alternative embodiment, while three fiducial implants 10 are the minimum necessary to define an internal coordinate system, there can be n fiducial implants 10, where n is greater than or equal to four and is an integer, that may be used. The advantage of using n fiducial implants 10 is that additional internal coordinate systems can be defined that result in increased clarity of images obtained from an imager by the proper choice of the coordinate system to maximize the same.

This is especially true with respect to the comparison of, for instance, an image from a magnetic resonance imager and an image of a CT imager concerning the same portion of a patient's anatomy. Depending on the distortion, if any, that is present in images that are obtained, three fiducial implants 10 can be picked from the n fiducial implants 10 that are present in a patient to provide the greatest clarity and image with respect to the patient. The internal coordinate system can be determined by choosing which three fiducial implants 10 of the n fiducial implants 10 provide an internal coordinate system which yields the clearest images or the best view of the portion of anatomy of interest. Additionally, once the three fiducial implants 10 are chosen of the n fiducial implants 10, it does not necessarily mean that each image must be produced with respect to the coordinate system defined by these three fiducial implants 10. Instead, as each image is produced with respect to a certain portion of the anatomy of a patient, the various coordinate systems that are present due to there being n fiducial implants 10 can be reviewed and for each image, the choice of the coordinate system that provides the most clarity can be chosen. Once the 3 fiducial implants 10 are chosen, then the internal coordinate system defined by them can be used as is described herein.

Obviously, numerous (additional) modifications and variations of the present invention are possible in light of the above teachings. It is therefore to be understood that within the scope of the appended claims, the invention may be practiced otherwise than as specifically described herein.

What is claimed is:

1. An apparatus for producing image slices of the human anatomy of a patient comprising:
   a. an imaging means for producing sliced images of a desired cross-section of the anatomy;
   b. a display means for displaying the images produced by said imaging means;
   c. means for defining a coordinate system fixed in time with respect to the human anatomy identifiable by said imaging means, wherein said means for defining a coordinate system includes n implantable fiducial implants, where $n \geq 4$ and is an integer, said means being hidden from the exterior of the anatomy but detectable by said imaging means;
   d. programmable data processing means cooperating with imaging means to obtain image slices during a first scan and to obtain image slices during a second scan substantially identical to the image slices of the first scan.

2. The apparatus according to claim 1 wherein each fiducial implant includes a first portion and a second portion, said first portion being configured to be detected by said imaging means, said second portion configured for temporarily fixed attachment to a patient.

* * * * *

UNITED STATES PATENT AND TRADEMARK OFFICE
CERTIFICATE OF CORRECTION

Page 1 of 2

PATENT NO. : 5,097,839
DATED : March 24, 1992
INVENTOR(S) : GEORGE S. ALLEN

It is certified that error appears in the above-identified patent and that said Letters Patent is hereby corrected as shown below:

| Column | Line | Corrections |
|---|---|---|
| 2 | 20 | After "size" insert --,--. |
| 3 | 50 | Change "image" to --imager--. |
| 5 | 48 | Change "is" to --are--. |
| 7 | 50 | After "bone" insert --to--. |
| 9 | 55 | Change "successful" to --successive--. |
| 9 | 59 | Change "the" (second occurrence) to --then--. |
| 10 | 48 | Change "R" to --`R--. |
| 10 | 49 | Change "R" to --`R--. |
| 10 | 50 | Change "R" to --`R-- (two occurrences). |
| 10 | 55 | Change "R" to --`R-- (two occurrences). |
| 10 | 56 | Change "R" to --`R--. |
| 10 | 57 | Change "R" to --`R--. |
| 10 | 62 | Change "R" to --`R--. |
| 10 | 63 | Change "R" to --`R--. |
| 10 | 64 | Change "R" to --`R-- (two occurrences). |
| 11 | 21-22 | Change "orthogonally" to --orthogonality--. |

UNITED STATES PATENT AND TRADEMARK OFFICE
CERTIFICATE OF CORRECTION

PATENT NO. : 5,097,839
DATED : March 24, 1992
INVENTOR(S) : GEORGE S. ALLEN It is certified that error appears in the above-identified patent and that said Letters Patent is hereby corrected as shown below:

| Column | Line | Corrections |
|---|---|---|
| 11 | 37 | Change "(A-k1)R=R" to --(A-k1)R=`R--. |
| 11 | 48 | After "nal" delete ","; after "matrices" insert --,--; change "K - + 1" to --k = +1--. |
| 11 | 50 | Change "The" to --This--; change "lead" to --leads--; before "diago-" insert --a--. |
| 11 | 54 | Change "R" to --`R-- (two occurrences). |
| 11 | 55 | Change "R" to --`R-- (two occurrences). |
| 11 | 56 | Change "R" to --`R-- (two occurrences). |
| 18 | 20 | After "with" insert --said--. |

Signed and Sealed this

Tenth Day of August, 1993

Attest:

MICHAEL K. KIRK

*Attesting Officer*     Acting Commissioner of Patents and Trademarks